US012247983B2

United States Patent
Wang

(10) Patent No.: US 12,247,983 B2
(45) Date of Patent: Mar. 11, 2025

(54) PROTEIN A CHROMATOGRAPHY-ELECTROSPRAY IONIZATION MASS SPECTROMETER

(71) Applicant: Regeneron Pharmaceuticals, Inc., Tarrytown, NY (US)

(72) Inventor: Shunhai Wang, Scarsdale, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 404 days.

(21) Appl. No.: 16/751,706

(22) Filed: Jan. 24, 2020

(65) Prior Publication Data

US 2020/0240999 A1 Jul. 30, 2020

Related U.S. Application Data

(60) Provisional application No. 62/796,820, filed on Jan. 25, 2019.

(51) Int. Cl.
| | |
|---|---|
| *G01N 33/68* | (2006.01) |
| *G01N 30/14* | (2006.01) |
| *G01N 30/72* | (2006.01) |
| *H01J 49/16* | (2006.01) |

(52) U.S. Cl.
CPC ......... *G01N 33/6848* (2013.01); *G01N 30/14* (2013.01); *G01N 30/7206* (2013.01); *G01N 30/7233* (2013.01); *G01N 30/7266* (2013.01); *G01N 33/6854* (2013.01); *H01J 49/165* (2013.01); *G01N 2560/00* (2013.01)

(58) Field of Classification Search
None
See application file for complete search history.

(56) References Cited

PUBLICATIONS

Karas, M. et al. Nano-electrospray ionization mass spectrometry: addressing analytical problems beyond routine, Fresenius J Anal Chem (2000) 366 :669-676 (Year: 2000).*

Canarelli S. et al., "On-line microdialysis of proteins with high-salt buffers for direct coupling of electrospray ionization mass spectrometry and liquid chromatography," Journal of Chromatography A., Elsevier, Amsterdam, NL, vol. 948, No. 1-2, Mar. 1, 2002, pp. 139-149.

Rabah Gahoual et al., "Detailed Characterization of Monoclonal Antibody Receptor Interaction Using Affinity Liquid Chromatography Hyphenated to Native Mass Spectrometry," Analytical Chemistry, vol. 89, No. 10, May 16, 2017; pp. 5404-5412.

Markus Haberger et al., "Rapid characterization of biotherapeutic proteins by size-exclusion chromatography coupled to native mass spectrometry," MABS, vol. 8, No. 2,Dec. 10, 2015, pp. 331-339.

Dhanashri Bagal et al., "Resolving Disulfide Structural Isoforms of IgG2 Monoclonal Antibodies by Ion Mobility Mass Spectrometry," Analytical Chemistry, vol. 82, No. 16, Aug. 15, 2010, pp. 6751-6755.

(Continued)

*Primary Examiner* — Xiaoyun R Xu
(74) *Attorney, Agent, or Firm* — BakerHostetler

(57) ABSTRACT

Methods and system for characterizing a protein using a chromatographic system having a protein A chromatography resin and electrospray ionization mass spectrometer run under native conditions are provided.

12 Claims, 3 Drawing Sheets

(56) References Cited

PUBLICATIONS

International Search Report PCT Application No. PCT/US2020/014961, International Filing Date Jan. 24, 2020, Date of Mailing May 11, 2020.

Kukrer B. et al. Mass spectrometric analysis of intact human monoclonal antibody aggregates fractionated by size-exclusion chromatography, Pharmaceutical research, 2010, V. 27, p. 2197-2204 (p. 2199).

Dumont E. et al. Cell Clone Selection Using the Agilent Bio-Monolith Protein A Column and LC/MS, Agilent Technologies Application Note, publication No. 5991-5124EN, 2014; p. 1-10.

Cuykens F., Clayes M. Optimization of a liquid chromatography method based on simultaneous electrospray ionization mass spectrometric and ultraviolet photodiode array detection for analysis of flavonoid glycosides. Rapid Communications in Mass Spectrometry, 2002, V. 16, No. 24, p. 2341-2348.

Chen W.H. et al. High performance liquid chromatography-tandem mass spectrometry method for ex vivo metabolic studies of a rhenium-labeled radiopharmaceutical for liver cancer. European Journal of Mass Spectrometry, 2014, V. 20, No. 5, p. 375-382.

\* cited by examiner

PROTEIN A CHROMATOGRAPHY-ELECTROSPRAY IONIZATION MASS SPECTROMETER

FIELD

The invention generally pertains to a method and system for characterizing at least one protein using a protein A chromatography and electrospray mass spectrometer.

BACKGROUND

Protein based biopharmaceutical products have emerged as important drugs for the treatment of cancer, autoimmune disease, infection and cardiometabolic disorders, and they represent one of the fastest growing product segments of the pharmaceutical industry.

Protein based biopharmaceutical products must meet very high standards of purity. There are several process-related impurities and product-related impurities that are found in biopharmaceuticals. These impurities do not have properties comparable to those of the desired product with respect to activity, efficacy, and safety. One example is post-translational modifications (PTMs) of the protein which profoundly affect protein properties relevant to their therapeutic application. These impurities could exhibit a different mode of action and potential toxicity or immunogenicity compared to the product. In addition, they can have a lower stability than the product which presents a higher risk for aggregation and immunogenicity. Despite the recent advances, the challenge to develop purity assay methods for quantitative evaluation of such impurities remains. Additionally, a key challenge in analytical method development for bispecific antibodies can be that the method must accurately and reproducibly detect impurities present at 2% or lower level relative to the main desired species. Therefore, it is important to monitor and characterize such impurities during different stages of drug development and production. Despite the importance of impurities for biological function, their study on a large scale has been hampered by a lack of suitable methods.

Analytical methods for purity assays must display sufficient accuracy and resolution to detect and quantify desired product and their impurities. Evaluation of impurities, such as PTMs in antibodies and homodimers in bispecific antibodies, can be difficult due to similarities between structural and physicochemical properties of such impurities and the desired product. Direct analysis of such impurities requires isolation of the desired product in a sufficiently large amount for the assay which is undesirable and only been possible in selected cases.

Thus, there is a long felt need in the art for a method and/or system for identifying and quantifying a protein—impurities and/or the desired product in a protein based biopharmaceutical product.

SUMMARY

Growth in the development, manufacture and sale of protein-based biopharmaceutical products has led to an increasing demand for characterizing the active pharmaceutical ingredient and presence of any impurities in the biopharmaceutical products.

Exemplary embodiments disclosed herein satisfy the aforementioned demands by providing methods and systems for characterizing at least one protein using a protein A chromatography and electrospray mass spectrometer.

This disclosure, at least in part, provides a method for identifying a protein in a sample. N one exemplary embodiment, the method for identifying a protein comprises contacting a sample including the protein to a chromatographic system having a protein A chromatography resin, washing said protein A chromatography resin using a mobile phase to provide an eluent including the protein and identifying the protein in said eluent using an electrospray ionization mass spectrometer.

In one aspect of this embodiment, the method for identifying a protein in a sample in a sample can comprise contacting a sample to a chromatographic system having a protein A chromatography resin, washing said protein A chromatography resin using a mobile phase to provide an eluent including the protein and identifying the protein in said eluent using an electrospray ionization mass spectrometer, wherein the chromatographic system is coupled with the electrospray ionization mass spectrometer.

In one aspect of this embodiment, the method for identifying a protein in a sample in a sample can comprise contacting a sample to a chromatographic system having a protein A chromatography resin, washing said protein A chromatography resin using a mobile phase to provide an eluent including the protein and identifying the protein in said eluent using a native electrospray ionization mass spectrometer, wherein the chromatographic system is coupled with the native electrospray ionization mass spectrometer.

In one aspect of this embodiment, the method for identifying a protein in a sample in a sample can comprise contacting about 10 μg to about 100 μg of a sample to a chromatographic system having a protein A chromatography resin.

In one aspect of this embodiment, the method for identifying a protein in a sample in a sample can comprise washing the protein A chromatography resin using a mobile phase that can be compatible with an electrospray ionization mass spectrometer.

In some specific exemplary embodiments, the method for identifying a protein in a sample in a sample can comprise washing the protein A chromatography resin using a mobile phase, wherein the mobile phase can be selected from ammonium acetate, ammonium bicarbonate, or ammonium formate, or combinations thereof.

In some specific exemplary embodiments, the method for identifying a protein in a sample in a sample can comprise washing the protein A chromatography resin using a mobile phase containing up to 600 mM total salt concentration.

In one aspect of this embodiment, the method for identifying a protein in a sample in a sample can comprise washing the protein A chromatography resin using a mobile phase with a flow rate of 0.2 ml/min to 0.4 ml/min.

In one aspect of this embodiment, the method for identifying a protein in a sample in a sample can comprise contacting the sample to a chromatographic system having a protein A resin with an additional functionality, wherein the protein can be an antibody.

In one aspect of this embodiment, the method for identifying a protein in a sample in a sample can comprise contacting the sample to a chromatographic system having a protein A resin, wherein the fragment can be a degradation product of an antibody.

In one aspect of this embodiment, the method for identifying a protein in a sample in a sample can comprise contacting the sample to a chromatographic system having a protein A resin, wherein the fragment can be a variant of an antibody.

In one aspect of this embodiment, the method for identifying a protein in a sample in a sample can comprise contacting the sample to a chromatographic system having a protein A chromatography resin, wherein the protein is an impurity.

In one aspect of this embodiment, the method for identifying a protein in a sample in a sample can comprise contacting the sample to a chromatographic system having a protein A resin, wherein the protein is a bispecific antibody.

In one aspect of this embodiment, the method for identifying a protein in a sample in a sample can comprise identifying the protein using a mass spectrometer, wherein the electrospray ionization mass spectrometer can be run under native conditions.

In one aspect of this embodiment, the method for identifying a protein in a sample in a sample can comprise identifying the protein using a mass spectrometer, wherein the electrospray ionization mass spectrometer can be a tandem mass spectrometer.

In one aspect of this embodiment, the method for identifying a protein in a sample in a sample can comprise identifying the protein using a mass spectrometer, wherein the electrospray ionization mass spectrometer can be a tandem mass spectrometer.

In one aspect of this embodiment, the method for identifying a protein in a sample in a sample can comprise identifying the protein using a mass spectrometer, wherein the electrospray ionization mass spectrometer can be a nano-electrospray ionization mass spectrometer.

In one aspect of this embodiment, the method for identifying a protein in a sample in a sample can comprise fluidly connecting a chromatographic system with an electrospray ionization mass spectrometer using a splitter with at least two paths to couple the electrospray ionization mass spectrometer to the chromatographic system.

In one aspect of this embodiment, the method for identifying a protein in a sample in a sample can comprise fluidly connecting a chromatographic system with an ultraviolet detector using a splitter with at least two paths.

In one aspect of this embodiment, the method for identifying a protein in a sample in a sample can comprise fluidly connecting a chromatographic system with an ultraviolet detector using a splitter with at least two paths.

In one aspect of this embodiment, the method for identifying a protein in a sample in a sample can comprise contacting a sample to a chromatographic system having a protein A chromatography resin, washing said protein A chromatography resin using a mobile phase to provide an eluent, wherein the said eluent can be introduced in the electrospray ionization mass spectrometer, wherein a flow rate of electrospray from the electrospray ionization is about 10 nL/min to about 50 nL/min.

In one aspect of this embodiment, the method for identifying a protein in a sample in a sample can comprise contacting a sample to a chromatographic system having a protein A chromatography resin, washing said protein A chromatography resin using a mobile phase to provide an eluent, wherein the eluent provided from washing protein A chromatography resin is introduced in an electrospray ionization mass spectrometer, wherein a spray voltage of the electrospray is about 0.8 kV to about 1.5 kV.

In one aspect of this embodiment, the method for identifying a protein in a sample can comprise contacting a sample, wherein the sample can comprise at least two proteins.

In one aspect of this embodiment, the method for identifying a protein in a sample can comprise contacting a sample, wherein the sample can be subjected to condition selected from the group consisting of hydrogen peroxide, oxidation, heat, ultraviolet light, cool-white light, or combinations thereof.

This disclosure, at least in part, provides a method for quantifying a protein in a sample. In one exemplary embodiment, the method for quantifying a protein in a sample comprises contacting a sample including the protein to a chromatographic system having a protein A chromatography resin, washing said protein A chromatography resin using a mobile phase to provide an eluent including the protein and quantifying the protein in said eluent using an electrospray ionization mass spectrometer.

In one aspect of this embodiment, the method for quantifying a protein in a sample can also quantify relative abundance of a protein in a sample.

In one aspect of this embodiment, the method for quantifying a protein in a sample in a sample can comprise contacting a sample to a chromatographic system having a protein A chromatography resin, washing said protein A chromatography resin using a mobile phase to provide an eluent including the protein and quantifying the protein in said eluent using an electrospray ionization mass spectrometer, wherein the chromatographic system is coupled with the electrospray ionization mass spectrometer.

In one aspect of this embodiment, the method for i quantifying a protein in a sample in a sample can comprise contacting about 10 μg to about 100 μg of a sample to a chromatographic system having a protein A chromatography resin.

In one aspect of this embodiment, the method for quantifying a protein in a sample in a sample can comprise washing the protein A chromatography resin using a mobile phase that can be compatible with an electrospray ionization mass spectrometer.

In some specific exemplary embodiments, the method for quantifying a protein in a sample in a sample can comprise washing the protein A chromatography resin using a mobile phase, wherein the mobile phase can be selected from ammonium acetate, ammonium bicarbonate, or ammonium formate, or combinations thereof.

In some specific exemplary embodiments, the method for quantifying a protein in a sample in a sample can comprise washing the protein A chromatography resin using a mobile phase containing up to 600 mM total salt concentration.

In one aspect of this embodiment, the method for quantifying a protein in a sample in a sample can comprise washing the protein A chromatography resin using a mobile phase with a flow rate of 0.2 ml/min to 0.4 ml/min.

In one aspect of this embodiment, the method for quantifying a protein in a sample in a sample can comprise contacting the sample to a chromatographic system having a protein A resin with an additional functionality, wherein the protein can be an antibody.

In one aspect of this embodiment, the method for quantifying a protein in a sample in a sample can comprise contacting the sample to a chromatographic system having a protein A resin, wherein the fragment can be a degradation product of an antibody.

In one aspect of this embodiment, the method for quantifying a protein in a sample in a sample can comprise contacting the sample to a chromatographic system having a protein A resin, wherein the fragment can be a variant of an antibody.

In one aspect of this embodiment, the method for quantifying a protein in a sample in a sample can comprise contacting the sample to a chromatographic system having a protein A chromatography resin, wherein the protein can be an impurity.

In one aspect of this embodiment, the method for quantifying a protein in a sample in a sample can comprise contacting the sample to a chromatographic system having a protein A resin, wherein the protein can be a bispecific antibody.

In one aspect of this embodiment, the method for quantifying a protein in a sample in a sample can comprise identifying the protein using a mass spectrometer, wherein the electrospray ionization mass spectrometer can be run under native conditions.

In one aspect of this embodiment, the method for quantifying a protein in a sample in a sample can comprise identifying the protein using a mass spectrometer, wherein the electrospray ionization mass spectrometer can be a tandem mass spectrometer.

In one aspect of this embodiment, the method for quantifying a protein in a sample in a sample can comprise identifying the protein using a mass spectrometer, wherein the electrospray ionization mass spectrometer can be a tandem mass spectrometer.

In one aspect of this embodiment, the method for quantifying a protein in a sample in a sample can comprise identifying the protein using a mass spectrometer, wherein the electrospray ionization mass spectrometer can be a nano-electrospray ionization mass spectrometer.

In one aspect of this embodiment, the method for quantifying a protein in a sample in a sample can comprise fluidly connecting a chromatographic system with an electrospray ionization mass spectrometer using a splitter with at least two paths to couple the electrospray ionization mass spectrometer to the chromatographic system.

In one aspect of this embodiment, the method for quantifying a protein in a sample in a sample can comprise fluidly connecting a chromatographic system with an ultraviolet detector using a splitter with at least two paths.

In one aspect of this embodiment, the method for quantifying a protein in a sample in a sample can comprise fluidly connecting a chromatographic system with an ultraviolet detector using a splitter with at least two paths.

In one aspect of this embodiment, the method for quantifying a protein in a sample in a sample can comprise contacting a sample to a chromatographic system having a protein A chromatography resin, washing said protein A chromatography resin using a mobile phase to provide an eluent, wherein the said eluent can be introduced in the electrospray ionization mass spectrometer, wherein a flow rate of electrospray from the electrospray ionization can be about 10 nL/min to about 50 nL/min.

In one aspect of this embodiment, the method for quantifying a protein in a sample in a sample can comprise contacting a sample to a chromatographic system having a protein A chromatography resin, washing said protein A chromatography resin using a mobile phase to provide an eluent, wherein the eluent provided from washing protein A chromatography resin is introduced in an electrospray ionization mass spectrometer, wherein a spray voltage of the electrospray can be about 0.8 kV to about 1.5 kV.

In one aspect of this embodiment, the method for quantifying a protein in a sample can comprise contacting a sample, wherein the sample can comprise at least two proteins.

In one aspect of this embodiment, the method for quantifying a protein in a sample can comprise contacting a sample, wherein the sample can be subjected to condition selected from the group consisting of deglycosylation, oxidation, heat, ultraviolet light, cool-white light, or combinations thereof.

This disclosure, at least in part, provides a system comprising a chromatographic column having a protein A chromatography resin and an electrospray ionization mass spectrometer.

In one exemplary embodiment, the system can comprise an electrospray ionization mass spectrometer capable of being coupled online a chromatographic column.

In one aspect of this embodiment, the system can comprise a chromatographic column having a protein A chromatography resin, wherein the chromatographic column is capable of receiving a mobile phase and a sample including a protein.

In one aspect of this embodiment, the system can comprise a chromatographic column capable of being coupled to an ultraviolet detector using a splitter.

In one aspect of this embodiment, the system can comprise a chromatographic column capable of being coupled to an ultraviolet detector using a splitter with at least three paths.

In one aspect of this embodiment, the system can comprise an electrospray ionization mass spectrometer capable of being run under native conditions.

In one aspect of this embodiment, the system can comprise a nano-electrospray ionization mass spectrometer capable of being run under native conditions.

In one aspect of this embodiment, the system can comprise a chromatographic column having a protein A chromatography resin and an electrospray ionization mass spectrometer, wherein the system is capable of identifying the protein.

In one aspect of this embodiment, the system can comprise a chromatographic column having a protein A chromatography resin and an electrospray ionization mass spectrometer, wherein the system can be capable of ranking protein A affinity of monoclonal antibody variants.

In one aspect of this embodiment, the system can comprise a chromatographic column having a protein A chromatography resin and an electrospray ionization mass spectrometer, wherein the protein A chromatography resin and the electrospray ionization mass spectrometer can be compatible with a mobile phase selected from ammonium acetate, ammonium bicarbonate, or ammonium formate, or combinations thereof.

In one aspect of this embodiment, the system can comprise a chromatographic column having a protein A chromatography resin, wherein the chromatographic column can be washed with a mobile phase with a flow rate of 0.2 ml/min to 0.4 ml/min.

In one aspect of this embodiment, the system can be capable of ranking the Protein A affinity of monoclonal antibody variants.

DETAILED DESCRIPTION

Figure 1:
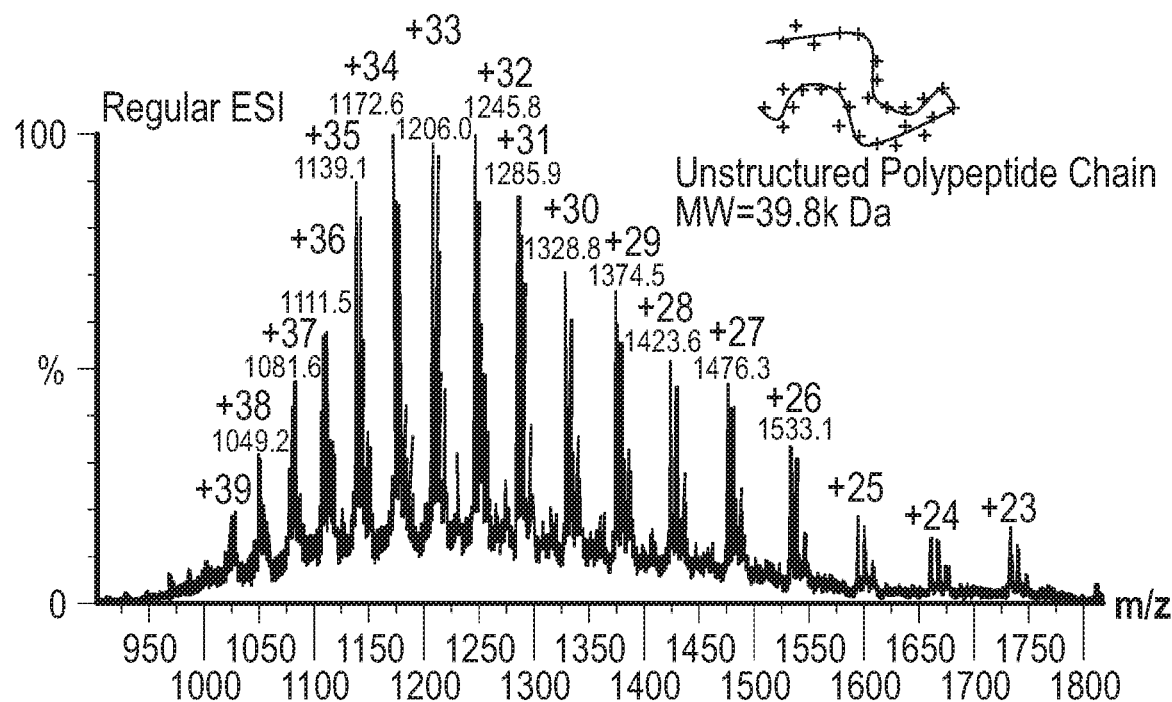
FIG. 1 shows spectra obtained from regular and native electrospray ionization mass spectrometry.
Figure 1:
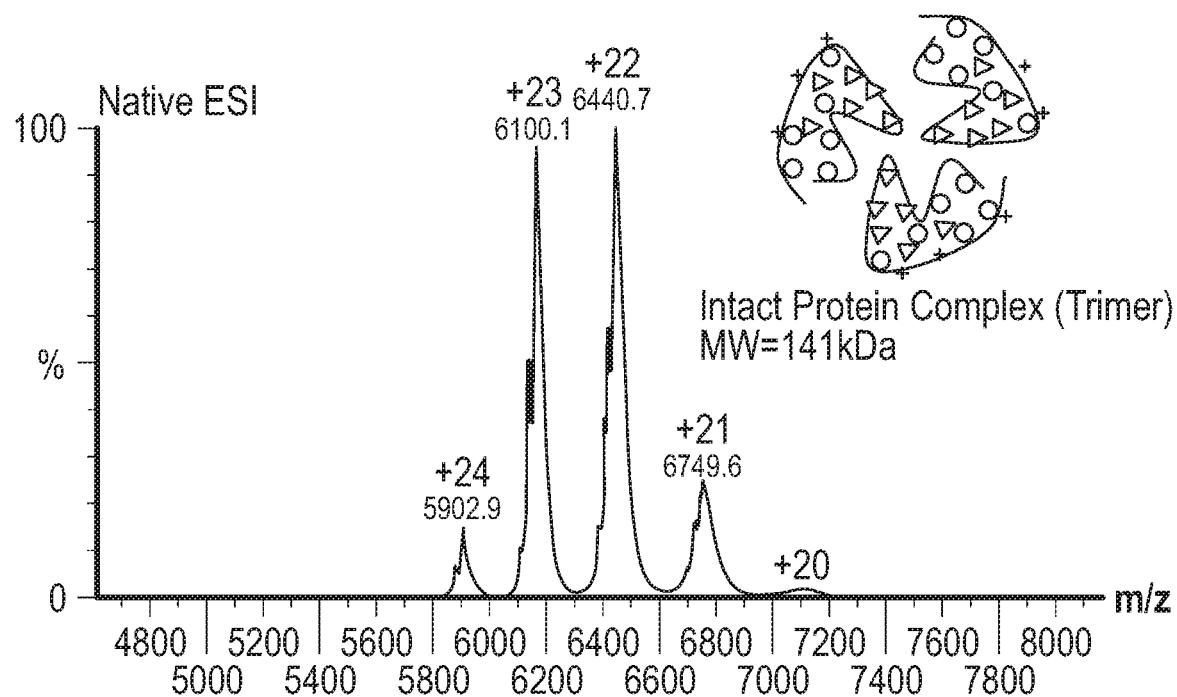

Recombinantly produced products can contain size variants (e.g., aggregates, fragments, degradation products, etc)

that are generated during manufacture and storage. Because aggregates and fragments may potentially affect immunogenicity and potency, their levels are typically monitored during lot release, stability, and characterization (Amy S. Rosenberg, *Effects of protein aggregates: An immunologic perspective,* 8 THE AAPS JOURNAL(2006)).

Monoclonal antibodies (mAbs) have emerged as one of the most important classes of biopharmaceutical products, although development of these molecules is long and arduous. Sensitive and high-throughput analytical methods that enhance process understanding and provide mechanistic insights for process improvement remain critical in the biopharmaceutical industry for the controlled production and purification of high quality therapeutic mAbs.

Protein A chromatography is one of the most critical steps in therapeutic mAb purification. It is even more so for the purification of bispecific mAbs using a strategy that relies on the different Protein A binding affinity between a bispecific product and monospecific impurities (Andrew D. Tustian et al., *Development of purification processes for fully human bispecific antibodies based upon modification of protein A binding avidity,* 8 MABS 828-838 (2016)). However, the mobile phase from the protein A chromatography column cannot be directly injected into the mass spectrometer and requires additional steps including a change in the mobile phase.

Considering the limitations of existing methods, a rapid online approach combining an affinity-based chromatography with native mass spectrometry, to evaluate the attenuation of Protein A binding interactions with mAb variants induced by modifications at the intact level, was developed. This method was then used to study the impact of different modifications on Protein A purification of therapeutic mAbs as well as bispecific mAbs.

Unless defined otherwise, all technical and scientific terms used herein have the same meaning as commonly understood by one of ordinary skill in the art to which this invention belongs. Although any methods and materials similar or equivalent to those described herein can be used in the practice or testing, particular methods and materials are now described. All publications mentioned are hereby incorporated by reference.

The term "a" should be understood to mean "at least one"; and the terms "about" and "approximately" should be understood to permit standard variation as would be understood by those of ordinary skill in the art; and where ranges are provided, endpoints are included.

Biopharmaceutical products are required to show high levels of potency, purity, and low level of structural heterogeneity. Structural heterogeneity often affects the bioactivity and efficacy of a drug. Therefore, characterizing and quantifying the therapeutic protein and/or the impurities is important in pharmaceutical drug development. Structural heterogeneity in a protein can arise from post-translational modifications as well as inherent chemical modifications during manufacturing and storage conditions. For proteins produced in the biotechnology industry, complementary separation techniques are necessary both to purify the target protein and to give an accurate picture of the quality of the final product. The complexity of the product eliminates the use of simple one-dimensional separation strategies.

As used herein, the term "protein" includes any amino acid polymer having covalently linked amide bonds. Proteins comprise one or more amino acid polymer chains, generally known in the art as "polypeptides." "Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. "Synthetic peptides or polypeptides" refers to a non-naturally occurring peptide or polypeptide. Synthetic peptides or polypeptides can be synthesized, for example, using an automated polypeptide synthesizer. Various solid phase peptide synthesis methods are known to those of skill in the art. A protein may contain one or multiple polypeptides to form a single functioning biomolecule. A protein can include any of bio-therapeutic proteins, recombinant proteins used in research or therapy, trap proteins and other chimeric receptor Fc-fusion proteins, chimeric proteins, antibodies, monoclonal antibodies, polyclonal antibodies, human antibodies, and bispecific antibodies. In another exemplary aspect, a protein can include antibody fragments, nanobodies, recombinant antibody chimeras, cytokines, chemokines, peptide hormones, and the like. Proteins may be produced using recombinant cell-based production systems, such as the insect bacculovirus system, yeast systems (e.g., *Pichia* sp.), mammalian systems (e.g., CHO cells and CHO derivatives like CHO-K1 cells). For a review discussing biotherapeutic proteins and their production, see Ghaderi et al., "Production platforms for biotherapeutic glycoproteins. Occurrence, impact, and challenges of non-human sialylation," (Biotechnol. Genet. Eng. Rev. (2012) 147-75). In some exemplary embodiments, proteins comprise modifications, adducts, and other covalently linked moieties. Those modifications, adducts and moieties include for example avidin, streptavidin, biotin, glycans (e.g., N-acetylgalactosamine, galactose, neuraminic acid, N-acetylglucosamine, fucose, mannose, and other monosaccharides), PEG, polyhistidine, FLAGtag, maltose binding protein (MBP), chitin binding protein (CBP), glutathione-S-transferase (GST) myc-epitope, fluorescent labels and other dyes, and the like. Proteins can be classified on the basis of compositions and solubility and can thus include simple proteins, such as, globular proteins and fibrous proteins; conjugated proteins, such as, nucleoproteins, glycoproteins, mucoproteins, chromoproteins, phosphoproteins, metalloproteins, and lipoproteins; and derived proteins, such as, primary derived proteins and secondary derived proteins.

In some exemplary embodiments, the protein can be an antibody, a bispecific antibody, a multispecific antibody, antibody fragment, monoclonal antibody, or combinations thereof.

The term "antibody," as used herein includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_{H2}$ and $C_H3$. Each light chain comprises a light chain variable region (abbreviated herein as LCVR or $V_L$) and a light chain constant region. The light chain constant region comprises one domain (C.sub.L1). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different exemplary embodiments, the FRs of the anti-big-ET-1 antibody (or antigen-binding portion thereof) may be identical to the human germline sequences, or may be naturally or artificially modified. An amino acid consensus sequence may be defined based on a side-by-side analysis of two or more CDRs. The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

As used herein, an "antibody fragment" includes a portion of an intact antibody, such as, for example, the antigen-binding or variable region of an antibody. Examples of antibody fragments include, but are not limited to, a Fab fragment, a Fab' fragment, a F(ab')2 fragment, a Fc fragment, a scFv fragment, a Fv fragment, a dsFv diabody, a dAb fragment, a Fd' fragment, a Fd fragment, and an isolated complementarity determining region (CDR) region, as well as triabodies, tetrabodies, linear antibodies, single-chain antibody molecules, and multi specific antibodies formed from antibody fragments. Fv fragments are the combination of the variable regions of the immunoglobulin heavy and light chains, and ScFv proteins are recombinant single chain polypeptide molecules in which immunoglobulin light and heavy chain variable regions are connected by a peptide linker. An antibody fragment may be produced by various means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains that are linked together, for example, by disulfide linkages. An antibody fragment may optionally comprise a multi-molecular complex.

The term "monoclonal antibody" as used herein is not limited to antibodies produced through hybridoma technology. A monoclonal antibody can be derived from a single clone, including any eukaryotic, prokaryotic, or phage clone, by any means available or known in the art. Monoclonal antibodies useful with the present disclosure can be prepared using a wide variety of techniques known in the art including the use of hybridoma, recombinant, and phage display technologies, or a combination thereof.

The term "Fc fusion proteins" as used herein include part or all of two or more proteins, one of which is an Fc portion of an immunoglobulin molecule, that are not fused in their natural state. Preparation of fusion proteins comprising certain heterologous polypeptides fused to various portions of antibody-derived polypeptides (including the Fc domain) has been described, e.g., by Ashkenazi et al., Proc. Natl. Acad. ScL USA 88: 10535, 1991; Byrn et al., Nature 344:677, 1990; and Hollenbaugh et al., "Construction of Immunoglobulin Fusion Proteins", in Current Protocols in Immunology, Suppl. 4, pages 10.19.1-10.19.11, 1992. "Receptor Fc fusion proteins" comprise one or more of one or more extracellular domain(s) of a receptor coupled to an Fc moiety, which in some embodiments comprises a hinge region followed by a CH2 and CH3 domain of an immunoglobulin. In some embodiments, the Fc-fusion protein contains two or more distinct receptor chains that bind to a single or more than one ligand(s). For example, an Fc-fusion protein is a trap, such as for example an IL-1 trap (e.g., Rilonacept, which contains the IL-1 RAcP ligand binding region fused to the IL-1R1 extracellular region fused to Fc of hIgG1; see U.S. Pat. No. 6,927,004, which is herein incorporated by reference in its entirety), or a VEGF Trap (e.g., Aflibercept, which contains the Ig domain 2 of the VEGF receptor Flt1 fused to the Ig domain 3 of the VEGF receptor Flk1 fused to Fc of hIgG1; e.g., SEQ ID NO:1; see U.S. Pat. Nos. 7,087,411 and 7,279,159, which are herein incorporated by reference in their entirety)

In some exemplary embodiments, the protein can be an impurity. In some specific exemplary embodiments, the protein can be a product-related impurity.

As used herein, the term "impurity" can include any undesirable protein present in the protein biopharmaceutical product. Impurity can include process and product-related impurities. The impurity can further be of known structure, partially characterized, or unidentified. Process-related impurities can be derived from the manufacturing process and can include the three major categories: cell substrate-derived, cell culture-derived and downstream derived. Cell substrate-derived impurities include, but are not limited to, proteins derived from the host organism and nucleic acid (host cell genomic, vector, or total DNA). Cell culture-derived impurities include, but are not limited to, inducers, antibiotics, serum, and other media components. Downstream-derived impurities include, but are not limited to, enzymes, chemical and biochemical processing reagents (e.g., cyanogen bromide, guanidine, oxidizing and reducing agents), inorganic salts (e.g., heavy metals, arsenic, nonmetallic ion), solvents, carriers, ligands (e.g., monoclonal antibodies), and other leachables. Product-related impurities (e.g., precursors, certain degradation products) can be molecular variants arising during manufacture and/or storage that do not have properties comparable to those of the desired product with respect to activity, efficacy, and safety. Such variants may need considerable effort in isolation and characterization in order to identify the type of modification(s). Product-related impurities can include truncated forms, modified forms, and aggregates. Truncated forms are formed by hydrolytic enzymes or chemicals which catalyze the cleavage of peptide bonds. Modified forms include, but are not limited to, deamidated, isomerized, mismatched S—S linked, oxidized, or altered conjugated forms (e.g., glycosylation, phosphorylation). Modified forms can also include any post-translational modification form. Aggregates include dimers and higher multiples of the desired product. (Q6B Specifications: Test Procedures and Acceptance Criteria for Biotechnological/Biological Products, ICH August 1999, U.S. Dept. of Health and Humans Services).

In some exemplary embodiments, the protein can be a post-translationally modified protein. In some specific exemplary embodiments, the post-translational modified protein can be either introduced by design or induced by stressors. Non-limiting examples of stressors include hydrogen peroxide, oxidation, heat, ultraviolet light, cool-white light, or combinations thereof.

As used herein, the general term "post-translational modifications" or "PTMs" refer to covalent modifications that polypeptides undergo, either during (co-translational modification) or after (post-translational modification) their ribosomal synthesis. PTMs are generally introduced by specific enzymes or enzyme pathways. Many occur at the site of a specific characteristic protein sequence (signature sequence) within the protein backbone. Several hundred PTMs have been recorded, and these modifications invariably influence some aspect of a protein's structure or function (Walsh, G. "Proteins" (2014) second edition, published by Wiley and Sons, Ltd., ISBN: 9780470669853). The various post-translational modifications include, but are not limited to, cleavage, N-terminal extensions, protein degradation, acylation of the N-terminus, biotinylation (acylation of lysine residues with a biotin), amidation of the C-terminal, glycosylation, iodination, covalent attachment of prosthetic groups, acetylation (the addition of an acetyl group, usually at the N-terminus of the protein), alkylation (the addition of an alkyl group (e.g. methyl, ethyl, propyl) usually at lysine or arginine residues), methylation, adenylation, ADP-ribosylation, covalent cross links within, or between, polypeptide chains, sulfonation, prenylation, Vitamin C dependent modifications (proline and lysine hydroxylations and carboxy terminal amidation), Vitamin K dependent modification wherein Vitamin K is a cofactor in the carboxylation of glutamic acid residues resulting in the formation of a γ-carboxyglutamate (a glu residue), glutamylation (covalent linkage of glutamic acid residues), glycylation (covalent linkage glycine residues), glycosylation (addition of a glycosyl group to either asparagine, hydroxylysine, serine, or threonine, resulting in a glycoprotein), isoprenylation (addition of an isoprenoid group such as farnesol and geranylgeraniol), lipoylation (attachment of a lipoate functionality), phosphopantetheinylation (addition of a 4'-phosphopantetheinyl moiety from coenzyme A, as in fatty acid, polyketide, non-ribosomal peptide and leucine biosynthesis), phosphorylation (addition of a phosphate group, usually to serine, tyrosine, threonine or histidine), and sulfation (addition of a sulfate group, usually to a tyrosine residue). The post-translational modifications that change the chemical nature of amino acids include, but are not limited to, citrullination (the conversion of arginine to citrulline by deimination), and deamidation (the conversion of glutamine to glutamic acid or asparagine to aspartic acid). The post-translational modifications that involve structural changes include, but are not limited to, formation of disulfide bridges (covalent linkage of two cysteine amino acids) and proteolytic cleavage (cleavage of a protein at a peptide bond). Certain post-translational modifications involve the addition of other proteins or peptides, such as ISGylation (covalent linkage to the ISG15 protein (Interferon-Stimulated Gene)), SUMOylation (covalent linkage to the SUMO protein (Small Ubiquitin-related MOdifier)) and ubiquitination (covalent linkage to the protein ubiquitin). See European Bioinformatics InstituteProtein Information ResourceSIB Swiss Institute of Bioinformatics, EUROPEAN BIOINFORMATICS INSTITUTE DRS—DROSOMYCIN PRECURSOR—DROSOPHILA MELANOGASTER (FRUIT FLY)—DRS GENE & PROTEIN, http://www.uniprot.org/docs/ptm-list (last visited Jan. 15, 2019) for a more detailed controlled vocabulary of PTMs curated by UniProt.

In some exemplary embodiments, the protein can be identified using a system comprising a protein A chromatography resin and a mass spectrometer.

As used herein, the term "chromatography" refers to a process in which a chemical mixture carried by a liquid or gas can be separated into components as a result of differential distribution of the chemical entities as they flow around or over a stationary liquid or solid phase.

As used herein, the term "Protein A" encompasses Protein A recovered from a native source thereof, Protein A produced synthetically (e.g. by peptide synthesis or by recombinant techniques), and variants thereof which retain the ability to bind proteins which have a $C_H2/C_H3$ region. Non-limiting examples of Protein A commercial manufacturers include Repligen, Pharmacia and Fermatech.

The Protein A is immobilized on a solid phase. By "solid phase" is meant a non-aqueous matrix to which the Protein A can adhere. The solid phase of interest herein can comprise a glass or silica surface. The solid phase may be a purification column or a discontinuous phase of discrete particles.

As used herein, the term "mass spectrometer" includes a device capable of identifying specific molecular species and measuring their accurate masses. The term is meant to include any molecular detector into which a polypeptide or peptide may be eluted for detection and/or characterization. A mass spectrometer can include three major parts: the ion source, the mass analyzer, and the detector. The role of the ion source is to create gas phase ions. Analyte atoms, molecules, or clusters can be transferred into gas phase and ionized either concurrently (as in electrospray ionization). The choice of ion source depends heavily on the application.

In some embodiments, the mass spectrometer is an electrospray-mass spectrometer.

As used herein, the term "electrospray ionization" or "ESI" refers to the process of spray ionization in which either cations or anions in solution are transferred to the gas phase via formation and desolvation at atmospheric pressure of a stream of highly charged droplets that result from applying a potential difference between the tip of the electrospray needle containing the solution and a counter electrode. There are generally three major steps in the production of gas-phase ions from electrolyte ions in solution. These are: (a) production of charged droplets at the ES infusion tip; (b) shrinkage of charged droplets by solvent evaporation and repeated droplet disintegrations leading to small highly charged droplets capable of producing gas-phase ions; and (c) the mechanism by which gas-phase ions are produced from very small and highly charged droplets. Stages (a)-(c) generally occur in the atmospheric pressure region of the apparatus.

As used herein, the term "electrospray infusion setup" refers to an electrospray ionization system that is compatible with a mass spectrometer used for mass analysis of protein. In electrospray ionization, an electrospray needle has its orifice positioned close to the entrance orifice of a spectrometer. A sample, containing the protein of interest, can be pumped through the syringe needle. An electric potential between the syringe needle orifice and an orifice leading to the mass analyzer forms a spray ("electrospray") of the solution. The electrospray can be carried out at atmospheric pressure and provides highly charged droplets of the solution. The electrospray infusion setup can include an electrospray emitter, nebulization gas, and/or an ESI power supply. The setup can optionally be automated to carry out sample aspiration, sample dispensing, sample delivery, and/or for spraying the sample.

In some exemplary embodiments, the electrospray ionization mass spectrometer can be a nano-electrospray ionization mass spectrometer.

The term "nanoelectrospray" or "nanospray" as used herein refers to electrospray ionization at a very low solvent flow rate, typically hundreds of nanoliters per minute of sample solution or lower, often without the use of an external solvent delivery. The electrospray infusion setup forming a nanoelectrospray can use a static nanoelectrospray emitter or a dynamic nanoelectrospray emitter. A static nanoelectrospray emitter performs a continuous analysis of small sample (analyte) solution volumes over an extended period of time. A dynamic nanoelectrospray emitter uses a capillary column and a solvent delivery system to perform chromatographic separations on mixtures prior to analysis by the mass spectrometer.

As used herein, the term "mass analyzer" includes a device that can separate species, that is, atoms, molecules, or clusters, according to their mass. Non-liming examples of mass analyzers that could be employed for fast protein sequencing are time-of-flight (TOF), magnetic/electric sector, quadrupole mass filter (Q), quadrupole ion trap (QIT), orbitrap, Fourier transform ion cyclotron resonance (FTICR), and also the technique of accelerator mass spectrometry (AMS).

In some exemplary embodiments, mass spectrometry can be performed under native conditions.

As used herein, the term "native conditions" or "native MS" or "native ESI-MS" can include a performing mass spectrometry under conditions that preserve no-covalent interactions in an analyte. For detailed review on native MS, refer to the review: Elisabetta Boeri Erba & Carlo Petosa, *The emerging role of native mass spectrometry in characterizing the structure and dynamics of macromolecular complexes*, 24 PROTEIN SCIENCE 1176-1192 (2015). Some of the distinctions between native ESI and regular ESI are illustrated in table 1 and FIG. 1 (Hao Zhang et al., *Native mass spectrometry of photosynthetic pigment-protein complexes*, 587 FEBS Letters 1012-1020 (2013)).

TABLE 1

|  | Native ESI | Regular ESI |
|---|---|---|
| Sample Solution | Aqueous solution water, ammonium acetate | Partial organic solution water, formic acid, acetonitrile/Methanol (pH 1-2) |
| Spray Condition | 10-50 nL/min Spray voltage 0.8-1.5 kV Temperatures 20-30° C. | 10-50 nL/min Spray voltage 0.8-1.5 kV Temperatures 20-30° C. |
| Salt Treatment | Offline Desalt | Online/Offline Desalt with RP-HPLC |
| Protein Concentration | 1-10 µM (complex) | <1 µM (subunit) |
| Output Information | Molecular weight of protein complex and subunit Non-covalent interactions Stoichiometry Structure | Molecular weight of a single subunit |

In some exemplary embodiments, the mass spectrometer can be a tandem mass spectrometer.

As used herein, the term "tandem mass spectrometry" includes a technique where structural information on sample molecules is obtained by using multiple stages of mass selection and mass separation. A prerequisite is that the sample molecules can be transferred into gas phase and ionized intact and that they can be induced to fall apart in some predictable and controllable fashion after the first mass selection step. Multistage MS/MS, or MS$^n$, can be performed by first selecting and isolating a precursor ion (MS$^2$), fragmenting it, isolating a primary fragment ion (MS$^3$), fragmenting it, isolating a secondary fragment (MS$^4$), and so on as long as one can obtain meaningful information or the fragment ion signal is detectable. Tandem MS have been successfully performed with a wide variety of analyzer combinations. What analyzers to combine for a certain application is determined by many different factors, such as sensitivity, selectivity, and speed, but also size, cost, and availability. The two major categories of tandem MS methods are tandem-in-space and tandem-in-time, but there are also hybrids where tandem-in-time analyzers are coupled in space or with tandem-in-space analyzers.

Exemplary Embodiments

Embodiments disclosed herein provide compositions, methods, and systems for the rapid characterization of proteins in a sample.

As used herein, the terms "include," "includes," and "including," are meant to be non-limiting and are understood to mean "comprise," "comprises," and "comprising," respectively.

This disclosure, at least in part, provides a method for identifying a protein in a sample comprising contacting a sample including the protein to a chromatographic system having a protein A chromatography resin, washing said protein A chromatography resin using a mobile phase to provide an eluent including the protein and identifying the protein in said eluent using an electrospray ionization mass spectrometer.

This disclosure, at least in part, provides a method for quantifying a protein in a sample comprising contacting a sample including the protein to a chromatographic system having a protein A chromatography resin, washing said protein A chromatography resin using a mobile phase to provide an eluent including the protein and quantifying the protein in said eluent using an electrospray ionization mass spectrometer.

This disclosure, at least in part, provides a method for quantifying relative abundance of a protein in a sample comprising contacting a sample including the protein to a chromatographic system having a protein A chromatography resin, washing said protein A chromatography resin using a mobile phase to provide an eluent including the protein and quantifying the protein in said eluent using an electrospray ionization mass spectrometer.

In some exemplary embodiments, the protein can be a monoclonal antibody.

In some exemplary embodiments, the protein can be a therapeutic antibody.

In some exemplary embodiments, the protein can be an immunoglobulin protein.

In some exemplary embodiments, the protein can be a bispecific antibody.

In some exemplary embodiments, the protein can be an antibody fragment formed on digestion of the antibody.

In one exemplary embodiment, the protein can be a post-translationally modified protein.

In one exemplary embodiment, the protein can be an antibody variant.

In yet another exemplary embodiment, the protein can be an impurity found in a biopharmaceutical product.

In another exemplary embodiment, the protein can be an impurity found during the manufacture of the biopharmaceutical product.

In some exemplary embodiments, the protein can be a digestion product of the antibody. The digestion product can be formed by a hydrolyzing agent. The hydrolyzing agent can include agents carrying out digestion using enzymatic or non-enzymatic digestion. The hydrolyzing agent can be an agent that can carry out digestion using enzymatic digestion and can include trypsin, endoproteinase Arg-C, endoproteinase Asp-N, endoproteinase Glu-C, outer membrane protease T (OmpT), immunoglobulin-degrading enzyme of *Streptococcus pyogenes* (IdeS), chymotrypsin, pepsin, thermolysin, papain, pronase, and protease from *Aspergillus Saitoi*. The hydrolyzing agent can also be an agent that can carry out digestion using non-enzymatic digestion and can include the use of high temperature, microwave, ultrasound, high pressure, infrared, solvents. The digestion product can be a product-related impurity.

In some exemplary embodiments, the protein can include Fab fragment, a Fab' fragment, a F(ab')2 fragment, a scFv fragment, a Fv fragment, a dsFv diabody, a dAb fragment, a Fd' fragment, a Fd fragment, and an isolated complementarity determining region (CDR) region, triabodies, tetrabodies, linear antibodies, single-chain antibody molecules, and multi specific antibodies formed from antibody fragments.

In some exemplary embodiments, the protein can have a pI in the range of about 4.5 to about 9.0.

In one exemplary embodiment, the protein can have a pI of about 4.5, about 5.0, about 5.5, about 5.6, about 5.7, about 5.8, about 5.9, about 6.0, about 6.1 about 6.2, about 6.3, about 6.4, about 6.5, about 6.6, about 6.7, about 6.8, about 6.9, about 7.0, about 7.1 about 7.2, about 7.3, about 7.4, about 7.5, about 7.6, about 7.7, about 7.8, about 7.9, about 8.0, about 8.1 about 8.2, about 8.3, about 8.4, about 8.5, about 8.6, about 8.7, about 8.8, about 8.9, or about 9.0.

In one exemplary embodiment, the number of proteins in the sample can be at least two.

In some exemplary embodiments, amount of protein in the sample loaded on the chromatographic system can range from about 10 µg to about 100 µg. In one exemplary embodiment, amount of protein in the sample loaded on the chromatographic system can be about 10 µg, about 12.5 µg, about 15 µg, about 20 µg, about 25 µg, about 30 µg, about 35 µg, about 40 µg, about 45 µg, about 50 µg, about 55 µg, about 60 µg, about 65 µg, about 70 µg, about 75 µg, about 80 µg, about 85 µg, about 90 µg, about 95 µg, or about 100 µg.

In some exemplary embodiments, the mobile phase used to elute the protein can be a mobile phase that can be compatible with a mass spectrometer.

In some exemplary embodiments, the mobile phase used to elute the protein can be a mobile phase that can include a volatile salt.

In some specific exemplary embodiments, the mobile phase can be ammonium acetate, ammonium bicarbonate, or ammonium formate, or combinations thereof.

In one exemplary embodiment, the total concentration of the mobile phase can range up to about 600 mM. In one exemplary embodiment, the total concentration of the mobile phase can be about 5 mM, about 6 mM, 7 mM, about 8 mM, 9 mM, about 10 mM, 12.5 mM, about 15 mM, 17.5 mM, about 20 mM, 25 mM, about 30 mM, 35 mM, about 40 mM, 45 mM, about 50 mM, 55 mM, about 60 mM, 65 mM, about 70 mM, 75 mM, about 80 mM, 75 mM, about 95 mM, 100 mM, about 1100 mM, 120 mM, about 150 mM, 140 mM, about 150 mM, 160 mM, about 170 mM, 180 mM, about 190 mM, 200 mM, about 225 mM, 250 mM, about 275 mM, 300 mM, about 325 mM, 350 mM, about 375 mM, 400 mM, about 425 mM, 450 mM, about 475 mM, 500 mM, about 525 mM, 550 mM, about 575 mM, or about 600 mM.

In some exemplary embodiments, the mobile phase can have a flow rate of about 0.1 ml/min to about 0.4 ml/min in the chromatographic system. In one exemplary embodiment, the flow rate of the mobile phase can be about 0.1 ml/min, about 0.15 ml/min, about 0.20 ml/min, about 0.25 ml/min, about 0.30 ml/min, about 0.35 ml/min, or about 0.4 ml/min.

In some exemplary embodiments, the flow rate in the electrospray ionization mass spectrometer can be about 10 nL/min to about 50 nL/min.

In some exemplary embodiments, the electrospray ionization mass spectrometer can have a spray voltage of about 0.8 kV to about 1.5 kV.

In some exemplary embodiments, identifying can include protein sequencing, protein de novo sequencing, identifying post-translational modifications, or comparability analysis, or combinations thereof.

In one exemplary embodiment, the electrospray ionization mass spectrometer can be a tandem mass spectrometer.

In another exemplary embodiment, the electrospray ionization mass spectrometer can be a nano-electrospray mass spectrometer.

It is understood that the methods are not limited to any of the aforesaid protein, fragment, impurity, and column and that the methods for identifying or quantifying may be conducted by any suitable means.

Figure 2:
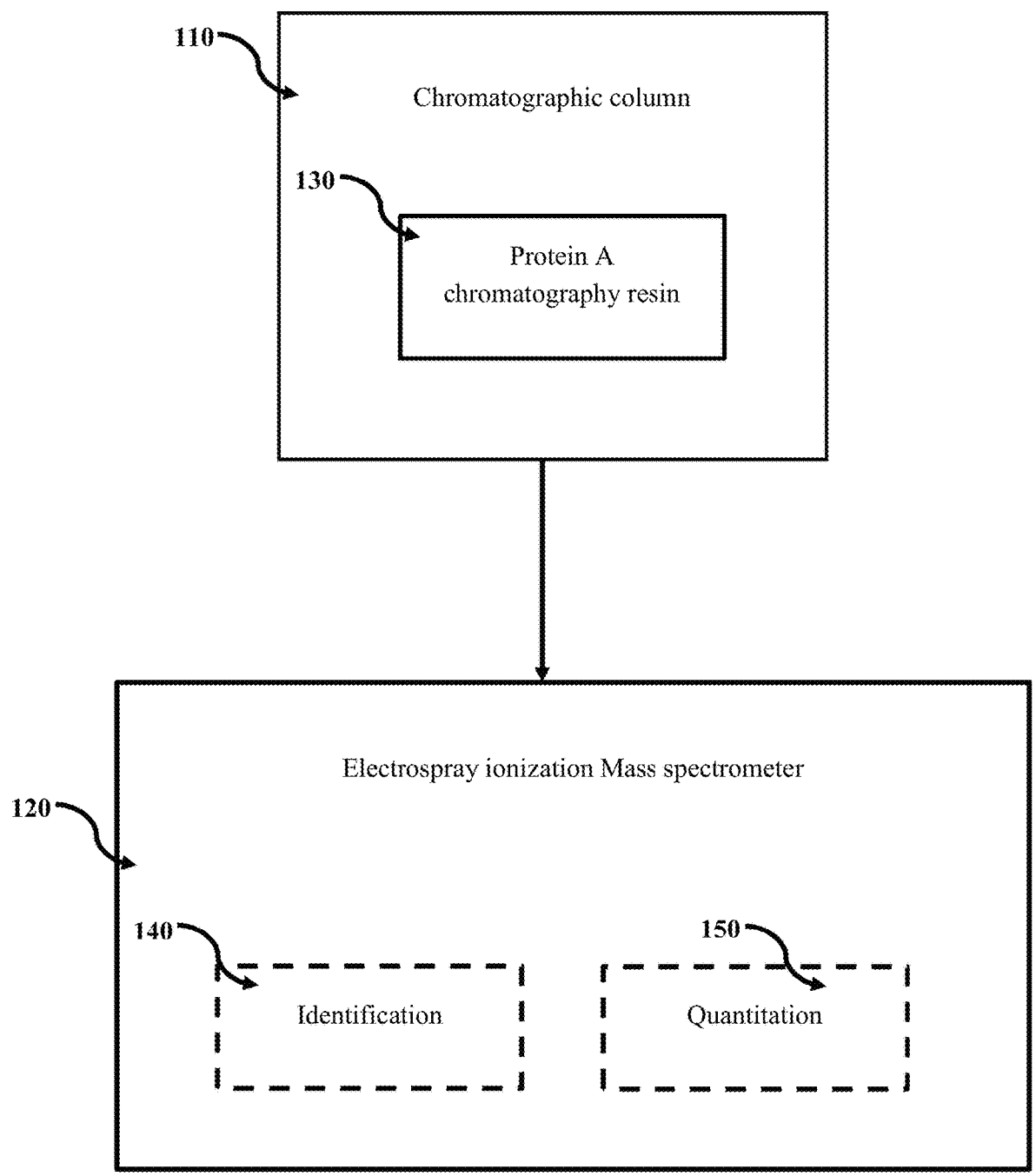
FIG. 2 shows a protein A chromatography-native electrospray mass spectrometry system according to an exemplary embodiment.

In some exemplary embodiments, the disclosure provides a system comprising a chromatographic column 110 capable of being washed using a mobile phase to provide an eluent and a mass spectrometer 120 coupled to the chromatographic column 110 (See FIG. 2).

In some exemplary embodiments, the chromatographic column 110 can comprise a protein A chromatographic resin 130.

FIG. 2 shows a chromatographic column comprising a protein A chromatographic resin 150, wherein the chromatographic column is fluidly connected or coupled to an electrospray ionization mass spectrometer 120 which can be run under native conditions.

In one exemplary embodiment, the chromatographic column 110 can be capable of being contacted with a sample including a protein.

In some exemplary embodiments, the amount of the sample that can be loaded on the chromatographic column 110 can range from about 10 µg to about 100 µg. In one exemplary embodiment, the amount of the sample that can be loaded on the chromatographic column 110 can be about 10 µg, about 12.5 µg, about 15 µg, about 20 µg, about 25 µg, about 30 µg, about 35 µg, about 40 µg, about 45 µg, about 50 µg, about 55 µg, about 60 µg, about 65 µg, about 70 µg, about 75 µg, about 80 µg, about 85 µg, about 90 µg, about 95 µg, or about 100 µg.

In some exemplary embodiments, the chromatographic column 110 can be capable of being washed with a mobile phase.

In some exemplary embodiments, the chromatographic column 110 can be capable of being washed with a mobile phase comprising a volatile salt.

In one exemplary embodiment, the mobile phase can be ammonium acetate, ammonium bicarbonate, or ammonium formate, or combinations thereof.

In one exemplary embodiment, the total concentration of the mobile phase that can be used to wash the chromatographic column 110 can range up to about 600 mM.

In one exemplary embodiment, the total concentration of the mobile phase that can be used to wash the chromatographic column 110 can be about 5 mM, about 6 mM, 7 mM, about 8 mM, 9 mM, about 10 mM, 12.5 mM, about 15 mM, 17.5 mM, about 20 mM, 25 mM, about 30 mM, 35 mM, about 40 mM, 45 mM, about 50 mM, 55 mM, about 60 mM, 65 mM, about 70 mM, 75 mM, about 80 mM, 75 mM, about 95 mM, 100 mM, about 1100 mM, 120 mM, about 150 mM, 140 mM, about 150 mM, 160 mM, about 170 mM, 180 mM, about 190 mM, 200 mM, about 225 mM, 250 mM, about 275 mM, 300 mM, about 325 mM, 350 mM, about 375 mM, 400 mM, about 425 mM, 450 mM, about 475 mM, 500 mM, about 525 mM, 550 mM, about 575 mM, or about 600 mM.

In another exemplary embodiment, the mobile phase that can be used with the chromatographic column 110 can have a flow rate of 0.1 ml/min to 0.4 ml/min.

In one exemplary embodiment, the flow rate of the mobile phase that can be used with the chromatographic column 110 can be about 0.1 ml/min, about 0.15 ml/min, about 0.20 ml/min, about 0.25 ml/min, about 0.30 ml/min, about 0.35 ml/min, or about 0.4 ml/min.

In some exemplary embodiments, the chromatographic column 110 can be capable of being coupled with a mass spectrometer 120.

In one exemplary embodiment, the mass spectrometer 120 can comprise a nanospray.

In some exemplary embodiments, the mass spectrometer 120 can be a tandem mass spectrometer.

In some exemplary embodiments, the mass spectrometer 120 can be an electrospray tandem mass spectrometer.

In some exemplary embodiments, the mass spectrometer 120 can be an nano-electrospray tandem mass spectrometer.

In some exemplary embodiments, the mass spectrometer 120 can be a native electrospray tandem mass spectrometer.

In some exemplary embodiments, the mass spectrometer 120 can be a native nano-electrospray tandem mass spectrometer.

In some exemplary embodiments, the system can be capable of identifying 140 and/or quantifying 150 a protein (as illustrated in FIG. 2). The protein can include an antibody, a monoclonal antibody, bispecific antibody, multispecific antibody, an antibody variant, a post-translationally modified antibody, a Fab fragment, a Fab' fragment, a F(ab')2 fragment, a scFv fragment, a Fv fragment, a dsFv diabody, a dAb fragment, a Fd' fragment, a Fd fragment, and an isolated complementarity determining region (CDR) region, triabodies, tetrabodies, linear antibodies, single-chain antibody molecules, and multi specific antibodies formed from antibody fragments.

In yet another exemplary embodiment, the system can be capable of identifying 140 and/or quantifying 150 a protein which can be an impurity found in a biopharmaceutical product.

In another exemplary embodiment, the system can be capable of identifying 140 and/or quantifying 150 a protein, wherein the protein can be an impurity found during the manufacture of the biopharmaceutical product.

In some exemplary embodiments, the system can be capable of identifying 140 and/or quantifying 150 a protein, wherein the protein can be a protein with a pI in the range of about 4.5 to about 9.0.

In some exemplary embodiments, the system can be capable of identifying 140 and/or quantifying 150 a protein, wherein the protein can be a product-related impurity.

In one exemplary embodiment, the system can be used to identify 140 and/or quantify 150 more than one protein. In one exemplary embodiment, the system can be used to identify 140 and/or quantify 150 two proteins.

Figure 3:
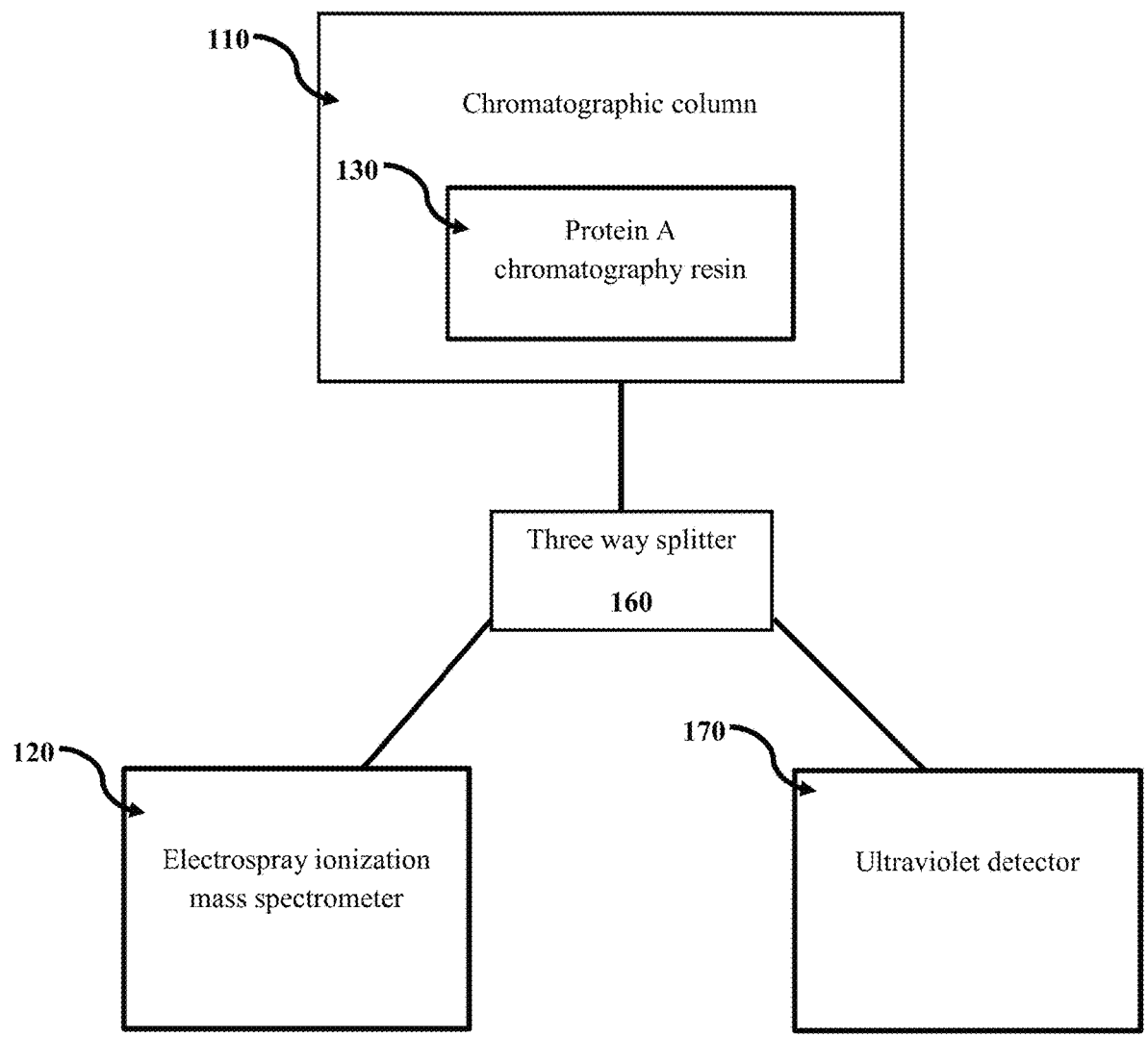
FIG. 3 shows a protein A chromatography-native nano electrospray mass spectrometry system according to an exemplary embodiment.

Another exemplary embodiment of the system in displayed in FIG. 3. A post-column splitter 160 with at least three paths is used to enable UV/MS dual detection. The low volume fraction can be directed to the MS 120 while the high volume fraction is transferred to the UV detector 170. Detection almost shares the same retention times. Fractions from the UV detector can be collected for sample recovery.

It is understood that the system is not limited to any of the aforesaid protein, impurity, mobile phase, mass spectrometer or chromatographic column.

The consecutive labeling of method steps as provided herein with numbers and/or letters is not meant to limit the method or any embodiments thereof to the particular indicated order.

Various publications, including patents, patent applications, published patent applications, accession numbers, technical articles and scholarly articles are cited throughout the specification. Each of these cited references is incorporated by reference, in its entirety and for all purposes, herein.

The disclosure will be more fully understood by reference to the following Examples, which are provided to describe the disclosure in greater detail. They are intended to illustrate and should not be construed as limiting the scope of the disclosure.

EXAMPLES

Exemplary implementations may be performed using an Acquity system (Waters, Milford, MA, USA) coupled to a UV detector and an electrospray ionization mass spectrometer (Thermo Exactive EMR, USA). The mass spectrometer may be operated in the positive resolution mode.

Sample preparation. Sample mAbs may be subjected to forced oxidation in the presence of 0.001%-0.02% (v/v) hydrogen peroxide ($H_2O_2$) for 24 hours.

System. Online Protein A affinity-based separation of monoclonal and bispecific antibody variants may be achieved using a Thermo Scientific MAbPac Protein A column (4×35 mm). A gradient from pH 7.5 to 3.0 in ammonium acetate-based mobile phases at a flow rate of 0.4 mL/min was used to elute differentially bound species. An analytical flow splitter (~1:400) may be used to reduce the post-column flow rate to the mass spectrometer to ~1 µL/min. A Thermo Q-Exactive UHMR mass spectrometer equipped with a Nanospray Flex™ Ion Source may be used for data acquisition.

Example 1

The retention time of different mAb variants, as determined by the extracted ion chromatograms (XICs), can be utilized to rank the Protein A affinity of mAb variants as a result of the different modifications.

Example 2

The method may also be applied to a mixture of a bispecific antibody (BsAb 1) and two corresponding monospecific mAbs (mAb1 and mAb2), which exhibit a sequential decrease in Protein A affinity.

Example 3

In addition, mAb samples after different treatments (e.g. deglycosylation, forced oxidation, and various stressed conditions) may be tested on this new technology platform.

What is claimed is:

1. A method for identifying at least one protein, said method comprising:
   contacting a sample including the protein to a chromatographic system having a protein A chromatography resin;

washing said protein A chromatography resin using a mobile phase to provide an eluate including the protein, wherein said eluate has a more acidic pH after washing; and identifying the protein in said eluate using an electrospray ionization mass spectrometer run under native conditions, wherein at least one splitter with at least three paths is used to couple said chromatographic system with said mass spectrometer and with an ultraviolet detector.

2. The method of claim 1, wherein the electrospray ionization mass spectrometer is coupled online to the chromatographic system having the protein A chromatography resin.

3. The method of claim 1, wherein the electrospray ionization mass spectrometer is a nano-electrospray ionization mass spectrometer.

4. The method of claim 1, wherein the mobile phase used to wash the protein A chromatography resin comprises a volatile salt.

5. The method of claim 1, wherein the eluate provided from washing the protein A chromatography resin is introduced in the electrospray ionization mass spectrometer, wherein a flow rate of electrospray from the electrospray ionization is about 10 nL/min to about 50 nL/min.

6. The method of claim 1, wherein the protein is a monoclonal antibody.

7. The method of claim 1, wherein the protein is a product related impurity.

8. The method of claim 1, wherein the protein is a bispecific antibody.

9. The method of claim 1, wherein the protein is an impurity.

10. The method of claim 1, wherein the protein is a monoclonal antibody variant.

11. The method of claim 1, wherein the sample comprises at least two proteins.

12. The method of claim 1, wherein the sample is subjected to condition selected from the group consisting of deglycosylation, oxidation, heat, ultraviolet light, cool-white light, or combinations thereof.

* * * * *